US010426637B2

(12) United States Patent
Tong et al.

(10) Patent No.: US 10,426,637 B2
(45) Date of Patent: Oct. 1, 2019

(54) EXOSKELETON ANKLE ROBOT

(71) Applicant: THE HONG KONG POLYTECHNIC UNIVERSITY, Hong Kong (HK)

(72) Inventors: Kai-Yu Tong, Hong Kong (HK); Ling Fung Yeung, Hong Kong (HK); Corinna Ursula Ockenfeld, Hong Kong (HK); Sze Kit Ho, Hong Kong (HK); Hon-Wah Wai, Hong Kong (HK); Man-Kit Pang, Hong Kong (HK)

(73) Assignee: THE HONG KONG POLYTECHNIC UNIVERSITY, Hong Kong (HK)

( * ) Notice: Subject to any disclaimer, the term of this patent is extended or adjusted under 35 U.S.C. 154(b) by 554 days.

(21) Appl. No.: 14/745,460

(22) Filed: Jun. 21, 2015

(65) Prior Publication Data

US 2016/0331557 A1    Nov. 17, 2016

Related U.S. Application Data

(60) Provisional application No. 62/159,955, filed on May 11, 2015.

(51) Int. Cl.
*A61F 2/66* (2006.01)
*A61H 1/02* (2006.01)
*A61H 3/00* (2006.01)

(52) U.S. Cl.
CPC ......... *A61F 2/6607* (2013.01); *A61H 1/0266* (2013.01); *A61H 3/00* (2013.01);
(Continued)

(58) Field of Classification Search
CPC ....... A61F 2/6607; A61H 3/00; A61H 1/0266; A61H 2201/165; A61H 2201/5061; A61H 2201/5097; A61H 2201/5084; A61H 2201/164; A61H 2201/5079; A61H 2201/5069; A61H 2201/5007; A61H 2230/625
See application file for complete search history.

(56) References Cited

U.S. PATENT DOCUMENTS 2,516,872 A    8/1950  Hauser
3,064,644 A   11/1962  Patterson
(Continued)

FOREIGN PATENT DOCUMENTS

CN    1586434 A     3/2005
CN   201168163 Y   12/2008
(Continued)

OTHER PUBLICATIONS

Translation for CN103610569.*
(Continued)

*Primary Examiner* — Megan Anderson
(74) *Attorney, Agent, or Firm* — Spruson & Ferguson (Hong Kong) Limited

(57) ABSTRACT

A portable electrical motor-driven exoskeleton ankle joint robot with gear transmission and control system which is intended to provide walking assistance in different speed and walking conditions to persons with disability in walking or muscle weakness or joint problem.

16 Claims, 18 Drawing Sheets

(52) U.S. Cl.
CPC .. *A61H 2201/164* (2013.01); *A61H 2201/165* (2013.01); *A61H 2201/5007* (2013.01); *A61H 2201/5061* (2013.01); *A61H 2201/5069* (2013.01); *A61H 2201/5079* (2013.01); *A61H 2201/5084* (2013.01); *A61H 2201/5097* (2013.01); *A61H 2230/625* (2013.01)

(56) References Cited

U.S. PATENT DOCUMENTS

| | | | |
|---|---|---|---|
| 4,314,227 | A | 2/1982 | Eventoff |
| 4,474,176 | A | 10/1984 | Farris |
| 4,601,206 | A | 7/1986 | Watson |
| 4,722,239 | A | 2/1988 | Fleck |
| 5,176,623 | A | 1/1993 | Stetman |
| 6,171,272 | B1 | 1/2001 | Akita |
| 6,350,246 | B1 | 2/2002 | DeToro |
| 6,666,796 | B1 | 9/2003 | MacCready |
| 6,752,774 | B2 | 6/2004 | Townsend |
| 7,485,074 | B2 | 2/2009 | Chen |
| 7,524,297 | B2 | 4/2009 | Shimada |
| 7,628,766 | B1 | 12/2009 | Kazerooni |
| 7,691,076 | B2 | 4/2010 | Castro |
| 7,771,373 | B2 | 8/2010 | Ido |
| 7,774,177 | B2 | 8/2010 | Dariush |
| 7,998,096 | B1 | 8/2011 | Skoog |
| 8,075,633 | B2 | 12/2011 | Herr |
| 8,079,967 | B2 | 12/2011 | Ikeuchi |
| 8,096,965 | B2 | 1/2012 | Goffer |
| 8,221,341 | B1 | 7/2012 | Al-Oboudi |
| 8,287,477 | B1 | 10/2012 | Herr |
| 8,353,854 | B2 | 1/2013 | Horst |
| 8,376,971 | B1 | 2/2013 | Herr |
| 8,382,694 | B2 | 2/2013 | Wenger |
| 8,439,852 | B2 | 5/2013 | Ebihara |
| 8,512,415 | B2 | 8/2013 | Herr |
| 8,591,438 | B2 | 11/2013 | Ikeuchi |
| 8,684,890 | B2 | 4/2014 | Bosecker |
| 8,720,831 | B2 * | 5/2014 | Jaeger ............... B64G 1/10 244/173.1 |
| 8,771,211 | B2 | 7/2014 | Bonutti |
| 8,777,884 | B2 | 7/2014 | DeHeer |
| 8,801,641 | B2 | 8/2014 | Kazerooni |
| 8,808,214 | B2 | 8/2014 | Herr |
| 8,814,815 | B2 | 8/2014 | DeHeer |
| 2003/0009308 | A1 | 1/2003 | Kirtley |
| 2004/0193318 | A1 | 9/2004 | Ito |
| 2005/0059908 | A1 | 3/2005 | Bogert |
| 2006/0084899 | A1 | 4/2006 | Verkade |
| 2006/0149338 | A1 | 7/2006 | Flaherty |
| 2007/0027409 | A1 | 2/2007 | Katoh |
| 2007/0049858 | A1 | 3/2007 | Agrawal |
| 2007/0123997 | A1 | 5/2007 | Herr |
| 2009/0043357 | A1 * | 2/2009 | Tong ............... A61B 5/112 607/49 |
| 2010/0076346 | A1 | 3/2010 | Abel |
| 2011/0071443 | A1 | 3/2011 | Weisz |
| 2011/0112447 | A1 | 5/2011 | Hsiao-Wecksler |
| 2011/0298343 | A1 | 12/2011 | Kim |
| 2013/0296741 | A1 | 11/2013 | Wiggin et al. |
| 2014/0002762 | A1 * | 1/2014 | Iwata ............... G09G 3/3648 349/42 |
| 2014/0109443 | A1 | 4/2014 | Fanchiang |
| 2014/0276264 | A1 | 9/2014 | Caires et al. |
| 2015/0374573 | A1 * | 12/2015 | Horst ............... A61H 3/00 602/16 |
| 2017/0027735 | A1 * | 2/2017 | Walsh ............... A61F 5/0102 |

FOREIGN PATENT DOCUMENTS

| | | |
|---|---|---|
| CN | 101623547 A | 1/2010 |
| CN | 201642750 U | 11/2010 |
| CN | 101596139 B | 1/2011 |
| CN | 102113949 A | 7/2011 |
| CN | 201888908 U | 7/2011 |
| CN | 202078502 U | 12/2011 |
| CN | 102961231 A | 3/2013 |
| CN | 103006357 A | 4/2013 |
| CN | 102068367 B | 5/2013 |
| CN | 102327173 B | 5/2013 |
| CN | 102225034 B | 7/2013 |
| CN | 102631275 B | 10/2013 |
| CN | 103584977 A | 2/2014 |
| CN | 103610567 A | 3/2014 |
| CN | 103610569 A | 3/2014 |
| CN | 103816029 A | 5/2014 |
| CN | 103610569 A | 6/2014 |

OTHER PUBLICATIONS

PCT International Search Report, dated May 5, 2016.
PCT written opinion, dated May 5, 2016.
Office Action of Taiwan Application No. 105113882 issued from the Taiwan Intellectual Property Office dated Jun. 16, 2017.
2nd Office Action of Taiwan Application No. 105113879 issued from the Taiwan Intellectual Property Office dated Apr. 11, 2018.

* cited by examiner

US 10,426,637 B2

EXOSKELETON ANKLE ROBOT

CROSS REFERENCE TO RELATED APPLICATION

Pursuant to 35 U.S.C. § 119(e), this is a non-provisional patent application which claims benefit from U.S. provisional patent application Ser. No. 62/159,955 filed May 11, 2015, and the disclosure of which is incorporated herein by reference.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to a portable electrical motor-driven exoskeleton ankle joint robot. In particular, the present intervention relates to a portable electrical motor-driven exoskeleton ankle joint robot with gear intended to provide walking assistance in different speed and walking conditions.

BACKGROUND

Due to aging population, the elderly population would be expected to increase every year, and more persons would have disability in walking or muscle weakness or joint problem. Stroke is a cerebrovascular accident that often occurs among the elderly population. Post-stroke survivors usually suffer from hemiplegia with severe weakness and loss of motor control over one side of the body, which significantly reduces their mobility and functional independency. Independent walking is an important function for good quality of life. However, weakness or impairment of the ankle muscles could significantly alter the gait pattern and impair the lower limb functionality. Thus, gait recovery is usually the first priority in stroke rehabilitation.

Drop foot is a common gait abnormality at the ankle joint that is caused by nerve injuries or neurological disorder such as stroke or multiple sclerosis. Patients would show muscle weakness at the dorsiflexors, and would often come with spasticity at the opposite plantar flexors. Abnormal gait pattern would increase energy expenditure and reduce balance ability in walking. Patient would be more prone to falling, tiredness, or joint limb pain.

Normal gait is a cyclic pattern that involves interaction between different lower limb body segments and joints working together to shift the center of mass of the ambulator forward step-by-step. During the normal gait, the ankle joint plays an important role in all aspect of locomotion, including motion control, shock absorption, stance stability, energy conservation, and propulsion. A gait cycle consists of two main parts: the stance phase and the swing phase. It begins with initial contact. The controlled loading response at heel strike absorbs shock and decelerates the foot before the foot completely landed. It provides gait stability during stance phase, when the ankle movement translates the body center of mass forward. At terminal stance, the ankle releases energy that stored in tendon and ligament of plantar flexor to provide propulsive force for push-off. In swing phase, the ankle dorsiflexor contracts to lift up the forefoot. It provides foot clearance and prevents the foot from stumbling into obstacles on the ground.

During walking of drop foot patients, the weak dorsiflexors fail to offer controlled loading response and shock absorption after heel strike. It leads to audible foot slap at initial contact. Weak plantar flexors and unstable ankle foot complex reduces stability during stance phase. Shorter stance phase and reduced propulsive power at push-off results in slower walking speed. In swing phase, the ankle cannot provide enough dorsiflexion moment to lift up the foot, so the foot is dragged on the ground. Stepping gait, hip hiking, and outward leg swinging are compensation mechanisms of drop foot. Patients tend to increase the knee and hip flexion during swing phase to allow more foot clearance. Ironically stroke survivors often have weak knee muscles. The result is an unstable and ineffective gait.

Effective gait training that achieves good therapeutic effect must satisfy these requirements: high intensity, high repeatability, long duration, and large task variation. It is encouraged that stroke patients to do more walking, especially in a outdoor setting where walking conditions may vary much. There are some gait assistive devices, such as U.S. Pat. No. 7,628,766 "Lower extremity enhancer" and U.S. Pat. No. 8,591,438 "Walk assisting device which defines a rigidity of portions thereof". They are targeted at providing bilateral gait assistance that is more suitable for completely paralyzed spinal cord injury patients, while stroke survivors who only need unilateral gait assistance are not served.

Gait rehabilitation usually would prescribe an ankle foot orthosis (AFO) to the stroke survivors. There are three types of AFO: passive, semi-active, and active. Passive AFO can be used to support the drop foot during swing phase. They are often rigid plastic that limits the ankle joint at the neutral 90 degrees to prevent plantar flexion. However, this kind of AFO imposes undesirable restriction to the ankle joint movement, thus unnatural gait. There are some articulated AFO with spring and dampers (U.S. Pat. No. 2,516,872A "Ankle brace", U.S. Pat. No. 3,064,644A "Lower leg brace", U.S. Pat. No. 5,176,623A "Multiple fixed angle orthopaedic appliance", U.S. Pat. No. 6,171,272B1 "Short leg brace", U.S. Pat. No. 6,350,246B1 "Ankle and foot therapeutic device", U.S. Pat. No. 7,691,076 "Articulated custom ankle-foot orthosis systems", U.S. Pat. No. 8,382,694 "Ankle-foot orthotic for treatment of foot drop", and US patent application no. 2006/0084899 "Hinged ankle brace"). Although they can control ankle joint movement without excessive restriction, they offer neither active assistance nor adaptation to different walking conditions. Semi-active AFO contains sensory feedback to determine different walking tasks, and then the joint impedance can be controlled using adjustable springs or dampers to support weak ankle dorsiflexion. However, these semi-active AFO cannot generate torque for active ankle joint assistance, especially at push-off. The power source comes from the wearer's gait but does not add energy to the system.

Existing active AFO have different types of motors and power transmission mechanisms. US patent application no. 2011/0112447A1 "Portable active fluid powered ankle-foot orthosis" is an active robot that uses pneumatic power to actuate the ankle joint. But the fluid container added weight to another body part and is bulky. U.S. Pat. No. 8,771,211 "Ankle orthosis" uses cam drive assembly and US patent application no. 2005/0059908 "Apparatus for assisting body movement" uses contraction for power transmission. U.S.

Pat. No. 8,808,214 "Active ankle foot orthosis" is an articulated AFO with adjustable joint impedance. These exoskeleton robots can be programmed to moderate drop foot walking according to gait phase, but they are too cumbersome to wear under clothes with unmodified footwear. Tethered power source also limits the device in clinical or laboratory utilities.

SUMMARY OF THE INVENTION

The present invention is a compact and portable exoskeleton ankle robot with a control algorithm that can provide gait assistance to the user with disability in walking or muscle weakness or joint problem in different walking conditions.

A first aspect of the presently claimed invention is to provide an exoskeleton robotic device for assisting gait of a user.

According to an embodiment of the presently claimed invention, an exoskeleton ankle robotic device comprises: a leg brace; a foot piece pivotally coupling to said leg brace at or proximal to an ankle position; an actuator coupling to said leg brace and said foot piece with an articulated joint, said actuator receiving power from a power source and generating torque driving said articulated joint to produce relative rotatory movement between said leg brace and said foot piece; a gear transmission system coupling to said articulated joint transmitting rotation axis of the actuator and optimized to a place where the device becomes compact and less cumbersome when wearing an unmodified shoe; at least one sensor for providing feedback of gait phase of a user; and a controller for receiving the feedback of gait phase from said at least one sensor and sending command to control said actuator for actively assisting gait of the user.

Preferably, said gear transmission system comprises at least one pair of gears, and said gears translate the axis of rotation to a location away from or proximal to said ankle position. Said location is anterior to a shank position of the user. Said at least one pair of gears has a gear ratio, and said gear ratio amplifies or diminishes a torque transmitting across said gear transmission system.

Preferably, said actuator comprises a servomotor providing torque control or position control to said articulated joint. Said actuator receives power from a battery.

Preferably, said leg brace and said foot piece comprises rigid and lightweight materials selected from the group consisting of carbon fiber, carbon composite, light metal, and plastic.

Preferably, said controller comprises a microprocessor and a memory. Said controller communicates with an external computing device through a wireless communication network.

Preferably, said at least one sensor comprises at least one force sensor coupling to said foot piece for generating a signal when receiving a force applying to at least one portion of said foot piece. Said at least one force sensor comprises a sensor selected from the group consisting of a force sensitive resistor, a force transducer, and a strain gauge.

Preferably, said at least one sensor comprises at least one motion sensor coupling to said leg brace and said foot piece for sensing a change in displacement and orientation of at least one portion of said device. Said at least one sensor comprises sensors selected from the group consisting of an accelerometer, a gyroscope, an angle encoder, a potentiometer, and a flex sensor.

A second aspect of the presently claimed invention is to provide a method for assisting gait of a user by a device.

According to an embodiment of the presently claimed invention, a method for assisting gait of a user by a device, comprises: a calibration; sensing a change in displacement and orientation of a leg brace coupling to a lower leg of the user, and a foot piece coupling to a foot of the user; sensing a plantar force applying to a front portion and a rear portion of said foot piece; determining a gait phase; classifying a walking speed and a walking condition using a control algorithm; and controlling an actuator to generate a predetermined torque profile for selectively assisting or braking an ankle joint movement of the user.

Preferably, said calibration comprises a standing calibration to obtain a set of predetermined thresholds, wherein the user stands on one leg for a predefined duration, in which the user switches the leg during said predefined duration to load or unload the foot. Said calibration comprises a walking calibration to obtain a set of predetermined thresholds, wherein the user walks for a predefined number of trials, in which said predefined number trials include one or more walking conditions, including different walking speeds and walking on different levels.

Preferably, said gait phase is a pre-swing phase, comprising a reduction in a plantar foot loading signal or an increase in an angular velocity signal of a shank of the user.

Preferably, said walking speed classification comprises a ratio between a kinematic gait parameter and a reference; wherein said reference is determined through said calibration. Said kinematic gait parameter is linear acceleration of shank of the user, or angular velocity of a thigh of the user at a pre-swing phase.

Preferably, said walking condition classification detects if a set of kinematic gait parameters exceeding a set of predetermined thresholds, wherein said set of predetermined thresholds comprises values that are determined through said calibration.

Preferably, said classification of walking conditions comprises overground walking, stair ascend, and stair descend. Said classification of stair descend condition comprises detecting high angular velocity in doriflexion and plantarflexion direction, low linear acceleration along the shank, and large ankle dorsiflexion of the shank of the user; and said classification of stair ascend condition comprises detecting low angular velocity and low angular acceleration of the shank of the user.

Preferably, said predetermined torque profile comprises a dorsiflexion moment that lasts until a loading response is detected; wherein said loading response comprises an increase in plantar foot loading signal.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

Figure 1:
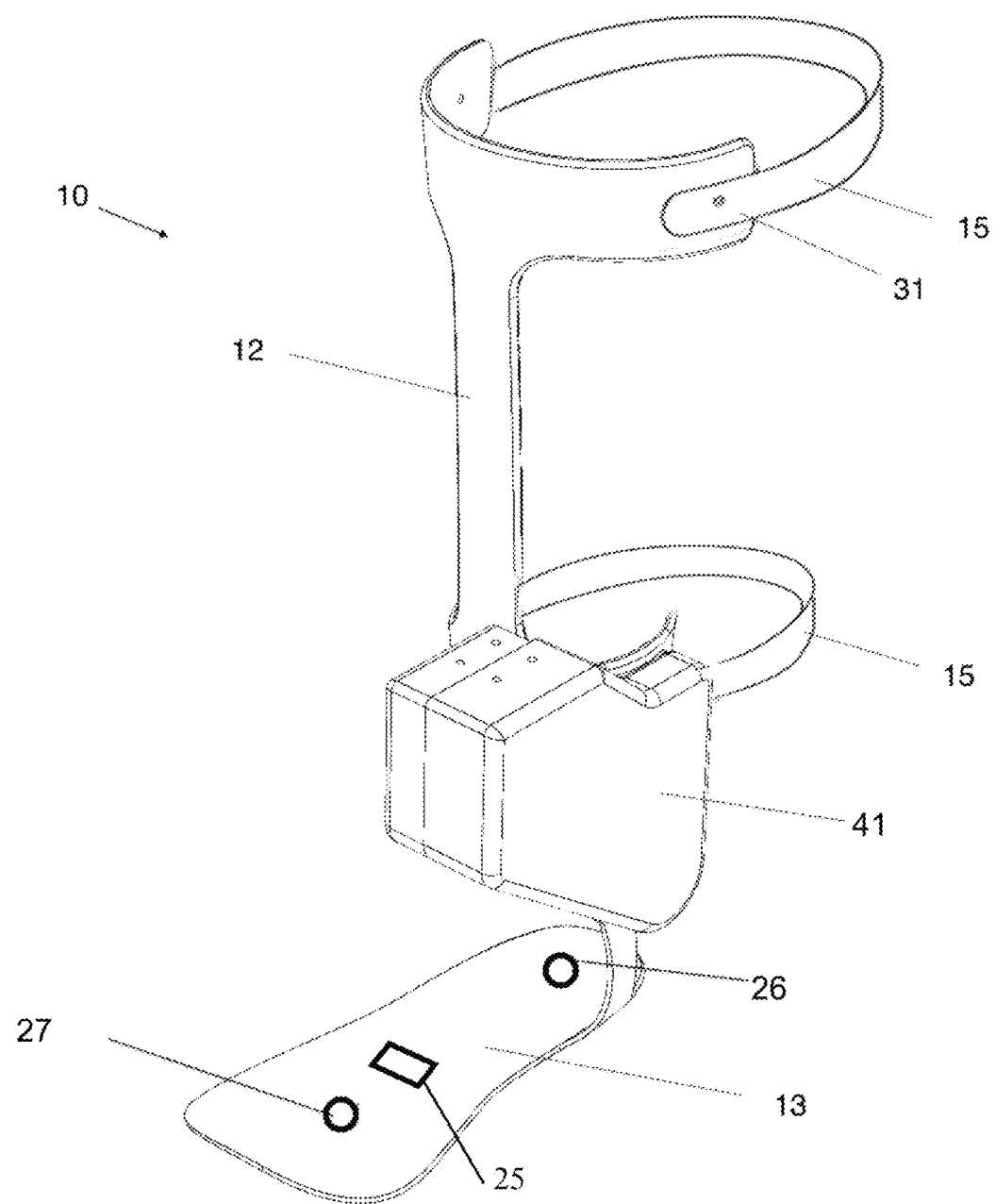
FIG. 1 is a front perspective view of the ankle robot according to an embodiment of the present invention.

In the following description, an exoskeleton ankle robotic device, and the corresponding embodiments are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

This invention is a compact and portable exoskeleton ankle robot with a control algorithm that can provide gait assistance to the user in different walking conditions. It is an ankle robot comprises a leg brace and a foot piece that pivotally coupled to the leg brace at or proximate to an ankle position. The ankle robot is preferably applying on the affected side of the user. The articulated ankle joint is coupled to an actuator through a gear transmission system. The actuator is preferably electrical rotatory servomotor that is capable of providing position and torque feedback. The gear transmission system is an important feature. Spur gears are meshed to transmit torque from the actuator to the articulated ankle joint. Multiple spur gears can be used for power transmission. Thus, the rotation axis of the actuator can be translated and optimized to a place where the device will become compact and less cumbersome. A preferred location of the actuator is the anterior shank, where the other movable parts of the device would usually not go in the way. Moreover, the actuator would not stick out sideways at the ankle joint that makes the device cumbersome and affect the user to wear his/her own unmodified shoe. Torque from the actuator can be amplified with a large gear ratio through this gear transmission system. The torque output requirement of the actuator can be minimized; so smaller actuator and power source can be used. The robot ankle system is preferably untethered for power supply or data communication. Wireless communication can be implemented. A non-limiting example of wireless system would be the Bluetooth communication protocol.

Lightweight composite materials, such as reinforced carbon fiber, can be used to fabricate the mechanical body. Electronic components, including microprocessor, power source, sensors, indicators, connection wires, and other essential electronic components can be embedded in the composite body. Embedded sensor system preferably provides kinetic and kinematic feedback about the gait pattern to actively assist different walking conditions of the user. The control algorithm implemented in the microprocessor can determine the walking intention of the user, including but not limited to determining different walking speeds and walking on different levels (level ground walking, uphill, downhill, upstairs, downstairs). The control algorithm classifies the walking conditions based on a set of predetermined thresholds. If certain set of kinetic and kinematic feedbacks from sensor exceeds the corresponding thresholds, the control algorithm computes and classifies the walking conditions. The set of predetermined thresholds can be determined by performing customized calibration for individual users before operation. Motor commands will be generated to control the actuator. Motor commands are preferably a predetermined torque or position profile of the actuator.

Control algorithm acquires input signals from the sensor system that is located on the affected side of the user. Motion sensors and force sensors are reasonable candidates for the sensing of useful kinematic gait parameters. Motion sensors are preferably accelerometers and gyroscopes. Force sensors are preferably foot switches or force sensitive resistors (FSR). Sensory feedbacks are preferably linear accelerations and angular velocities of the shank body segment in 3-dimension (x, y, z), and plantar foot loading patterns under the locations of the heel and the toe. Servomotor feedback signal for joint angle could be utilized in the control algorithm too.

Control algorithm identifies the walking intention of the wearer in real-time using the kinematic gait parameters acquired from the sensor system in the pre-swing phase of the gait cycle. The following is a working example of the control algorithm. However, the inventors want to emphasize that it is a non-limiting example of how to utilize sensor feedback of kinematic gait parameters to implement the control algorithm for walking intention identification. Pre-swing phase is the instant indicating the transition between the stance and the swing phases. The force sensor can identify this particular instant. For gait initiation, including stand-to-walk movement or beginning a cyclic gait pattern, the user can initialize the walking by shifting the body weight onto the unaffected leg while it is stepping forward. The result is a reduction in plantar foot loading in the affected side and the increase in angular velocity of the shank in the z-direction, i.e. perpendicular to the sagittal plane for the ankle dorsiflexion and plantarflexion with positive direction at dorsiflexion. At the pre-swing phase, the walking speed can be determined from a ratio between: the linear acceleration of the shank in the x-direction and a reference, i.e. in the forward walking direction; or the angular velocity of the shank and a reference. The linear acceleration x and the walking speed are usually in a linear proportional relationship. The ankle joint angle, linear accelerations x and y, and the angular velocity in the z-direction of the shank in the pre-swing phase could discriminate stair ascent/descent from over-ground walking. For instance, low angular velocity in the z-direction with little knee flexion and low linear acceleration in x-direction, indicates the stair ascend movement; high angular velocity in the z-direction, higher linear acceleration in the x-direction, and large ankle dorsiflexion are the indicators for the stair descend movement with the accelerometer is tilted downward; otherwise over-ground walking.

After the walking intention is identified at the pre-swing phase, the controller generates a pre-determined motor profile of torque or joint position that would be transmitted to control the actuator. The motor profile is designed to assist ankle motion during swing phase, which includes but not limited to active assistance of plantar flexion in push-off, active assistance of dorsiflexion throughout the swing phase, and controlled dorsiflexion at initial contact and loading response. The motor profile would be different for different identified walking intention, and would also vary between individual wearer. Thus the profile could be customized for each wearer by doing calibration before operation. The motor profile controls the actuation in the period from the pre-swing phase to the initial contact. Initial contact is detected when the swinging foot is loaded onto the ground, which leads to an increase in plantar foot loading. After the initial contact, the ankle joint would be free to move until the next pre-swing phase is detected and triggered.

Figure 2:
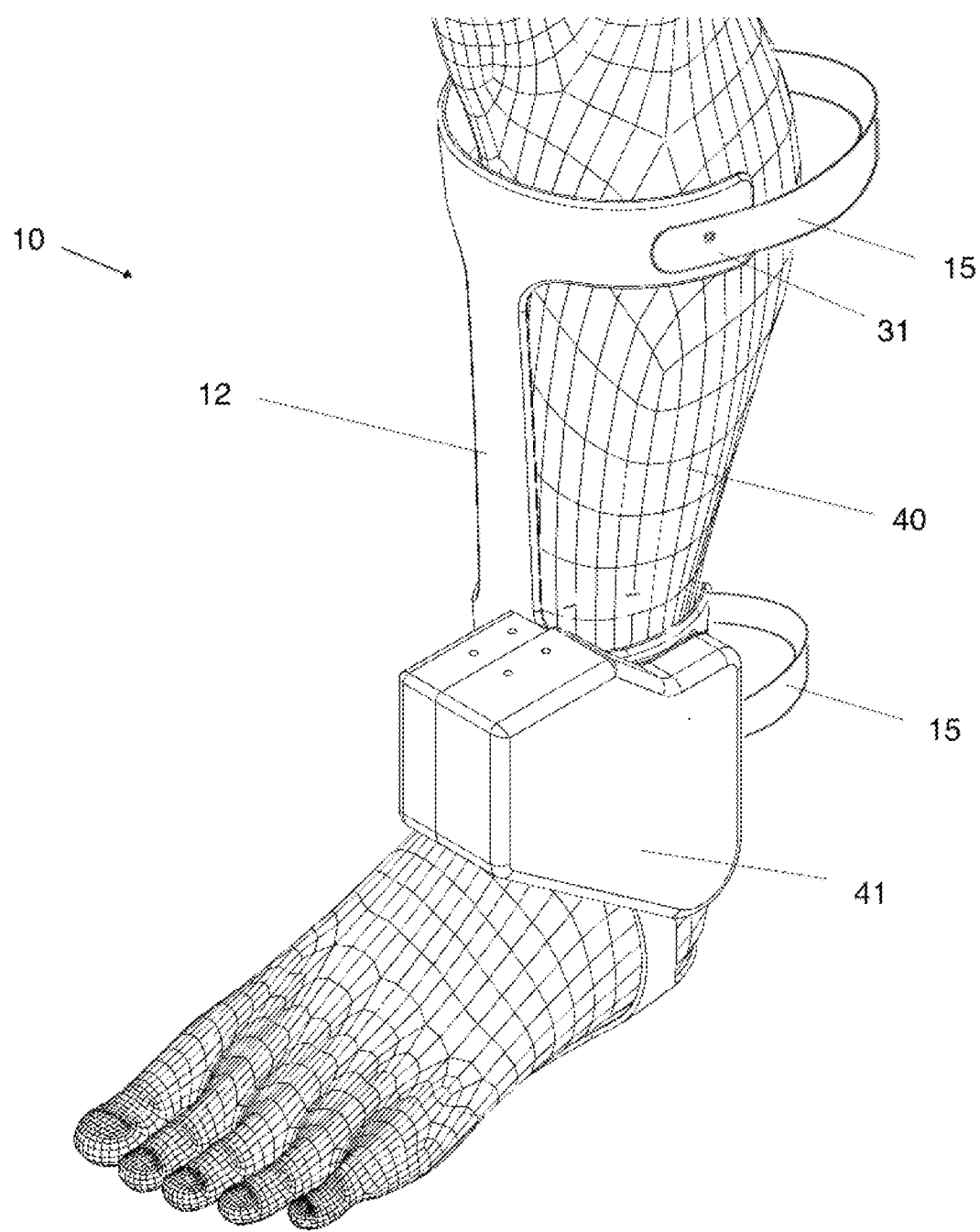
FIG. 2 shows the ankle foot complex of the user placed inside the ankle robot of FIG. 1.
Figure 3:
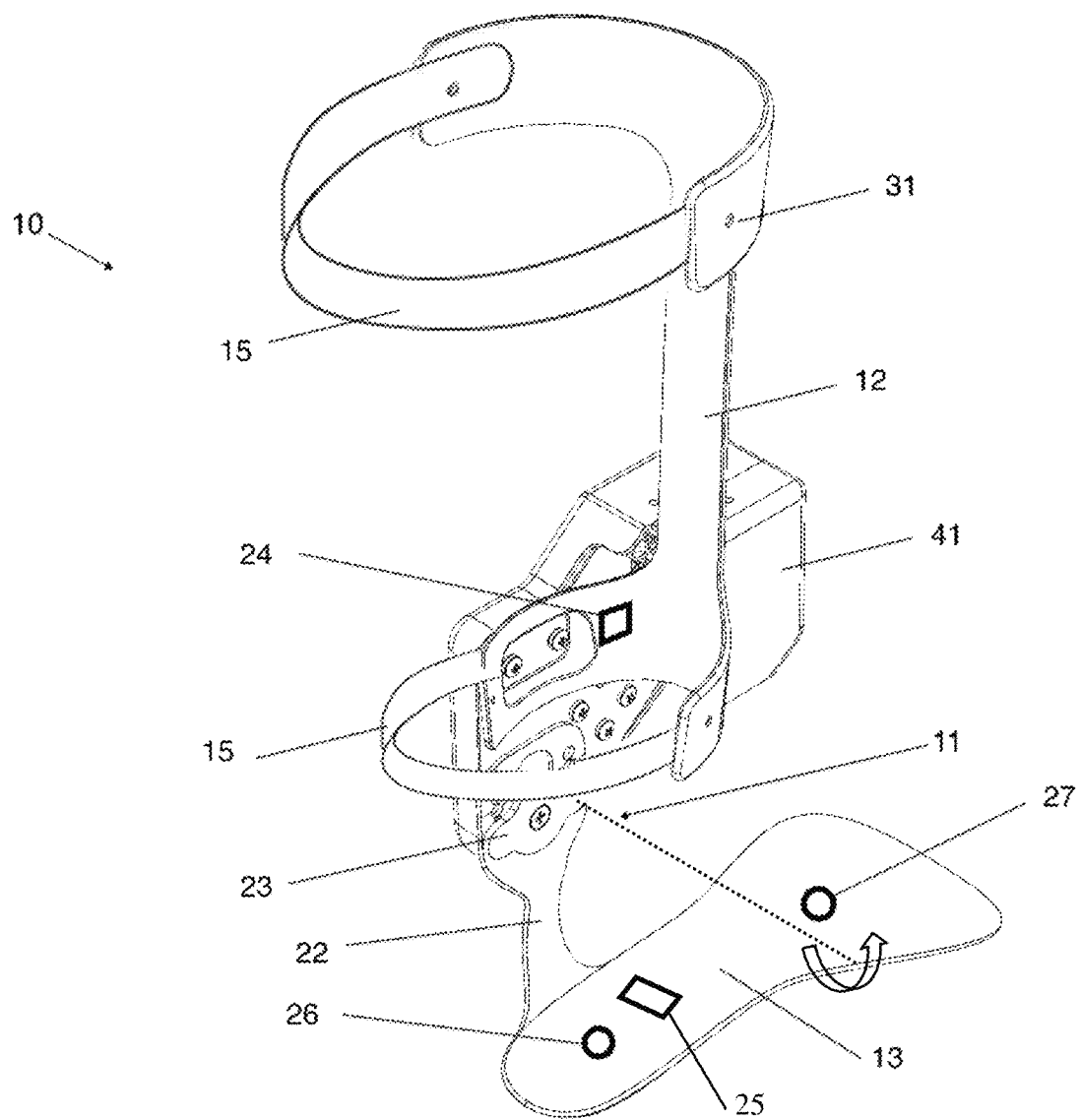
FIG. 3 is a rear perspective view of the ankle robot of FIG. 1.
Figure 4:
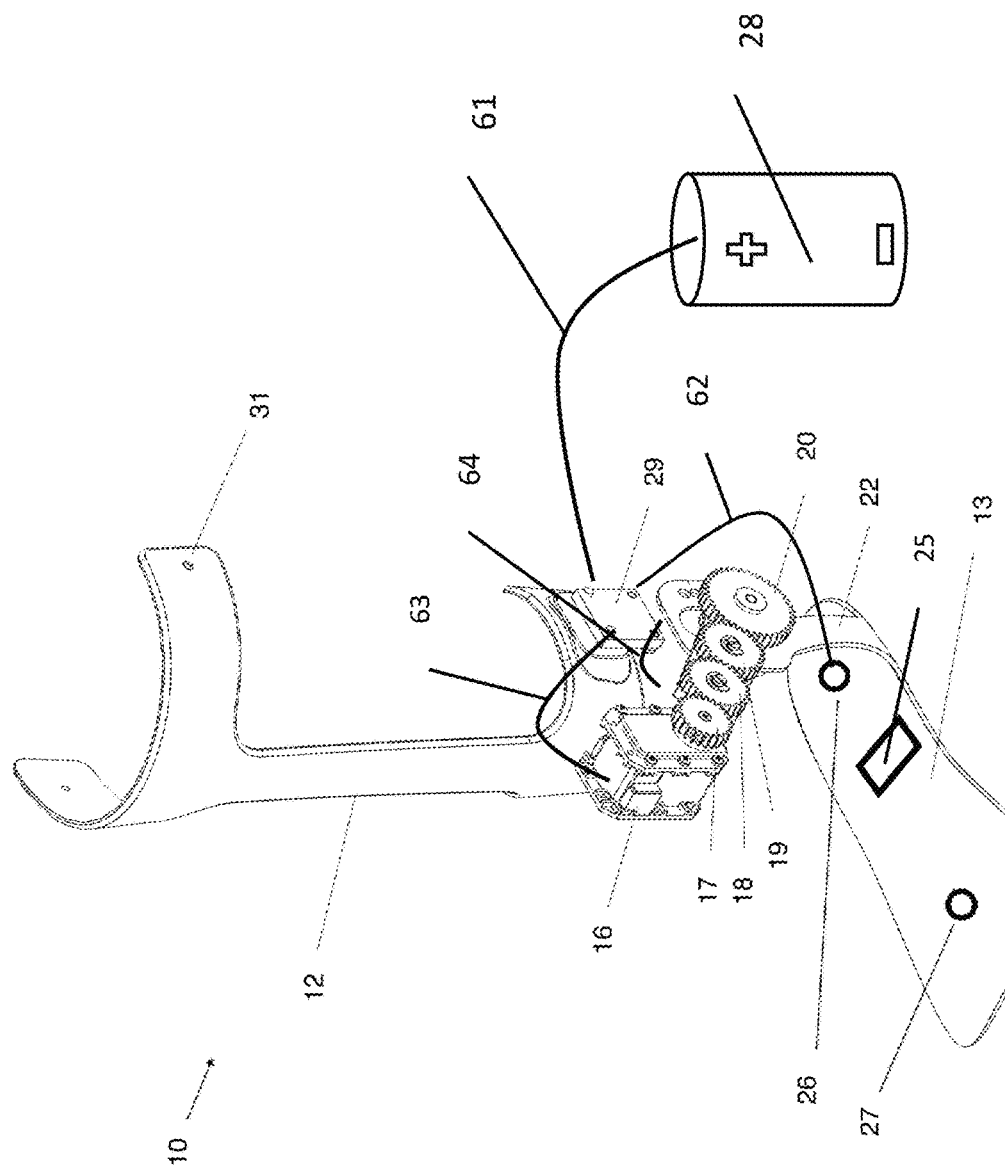
FIG. 4 shows the configuration of the gear transmission system according to an embodiment of the present invention.
Figure 5:
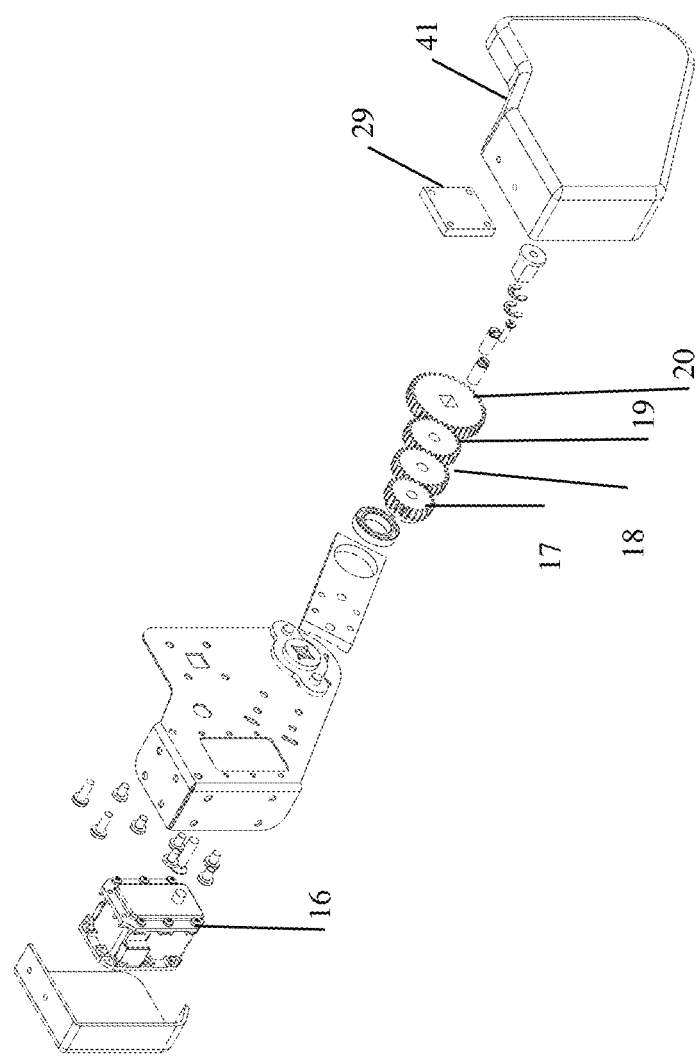
FIG. 5 is an exploded view of the control box of the ankle robot according to an embodiment of the present invention.
Figure 6:
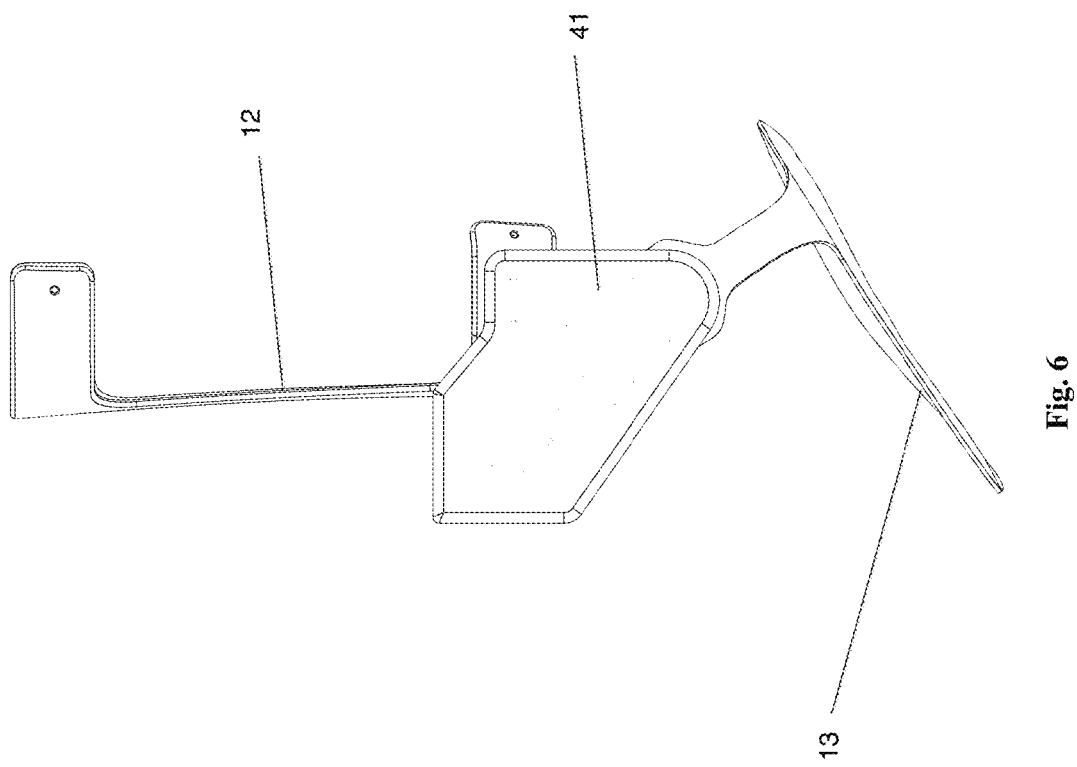
FIG. 6 is a side view of the ankle robot of FIG. 1 during ankle plantar flexion.
Figure 7:
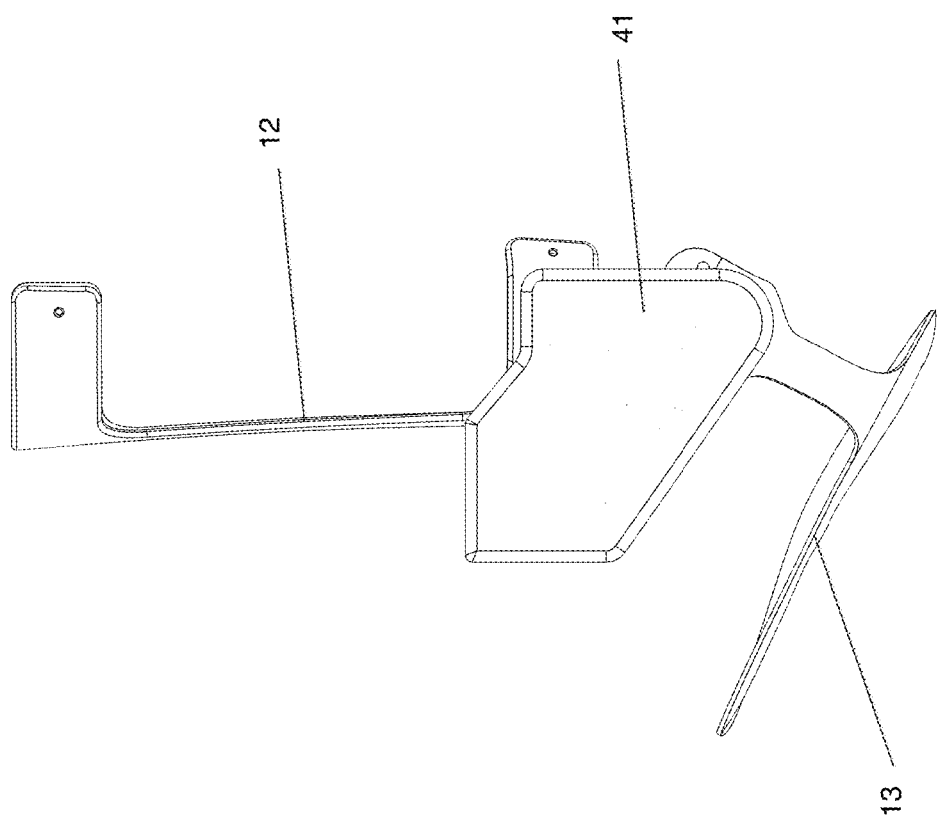
FIG. 7 is a side view of the ankle robot of FIG. 1 during ankle dorsiflexion.
Figure 8:
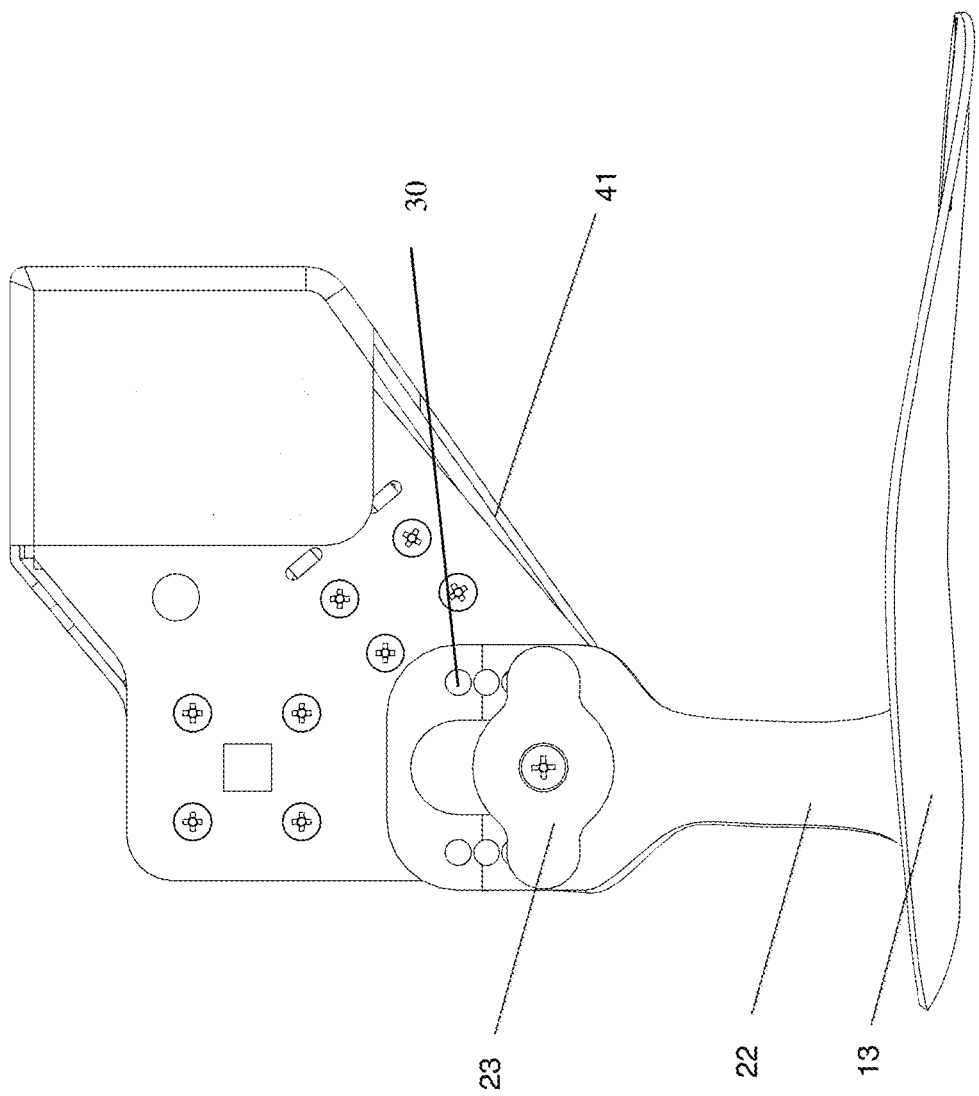
FIG. 8 is a side view of the articulated joint of the ankle robot of FIG. 3, showing the adjustment of minimum height of ankle joint.
Figure 9:
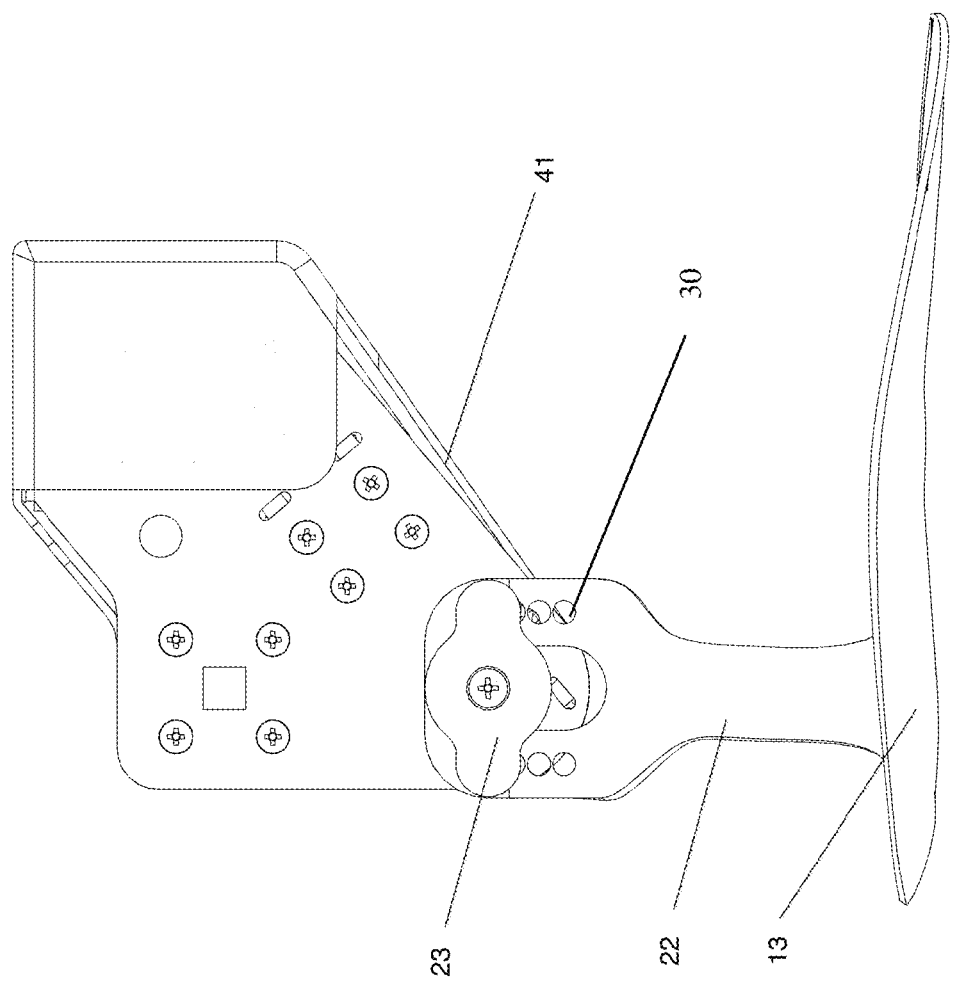
FIG. 9 is a side view of the articulated joint of the ankle robot of FIG. 3, showing the adjustment of maximum height of ankle joint.
Figure 10:
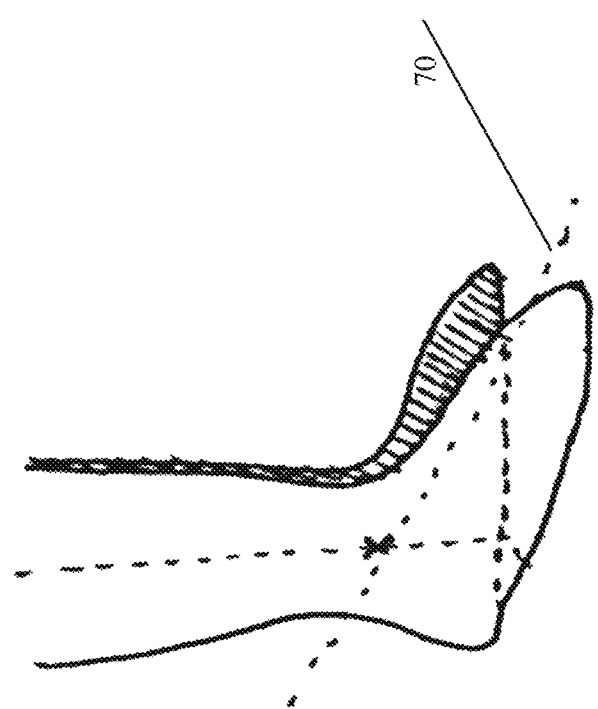
FIG. 10 shows healthy ankle and drop foot.
Figure 11:
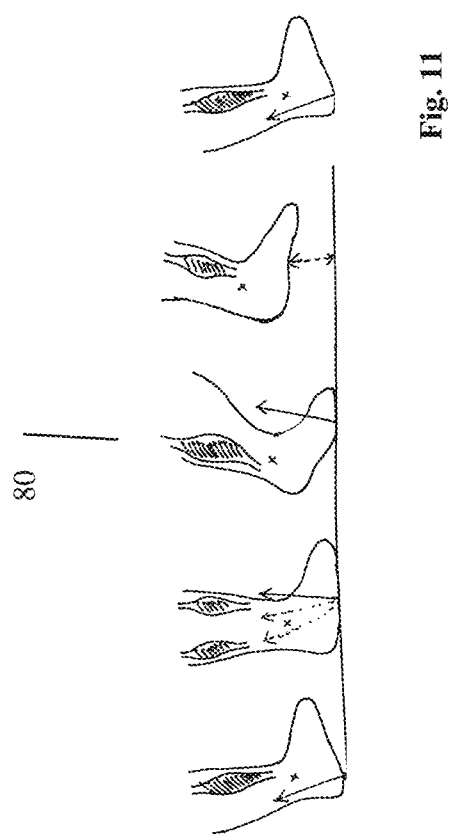
FIG. 11 shows normal gait cycle at the ankle joint, with indications of moment vector and the muscle contraction according to an embodiment of the present invention.
Figure 12:
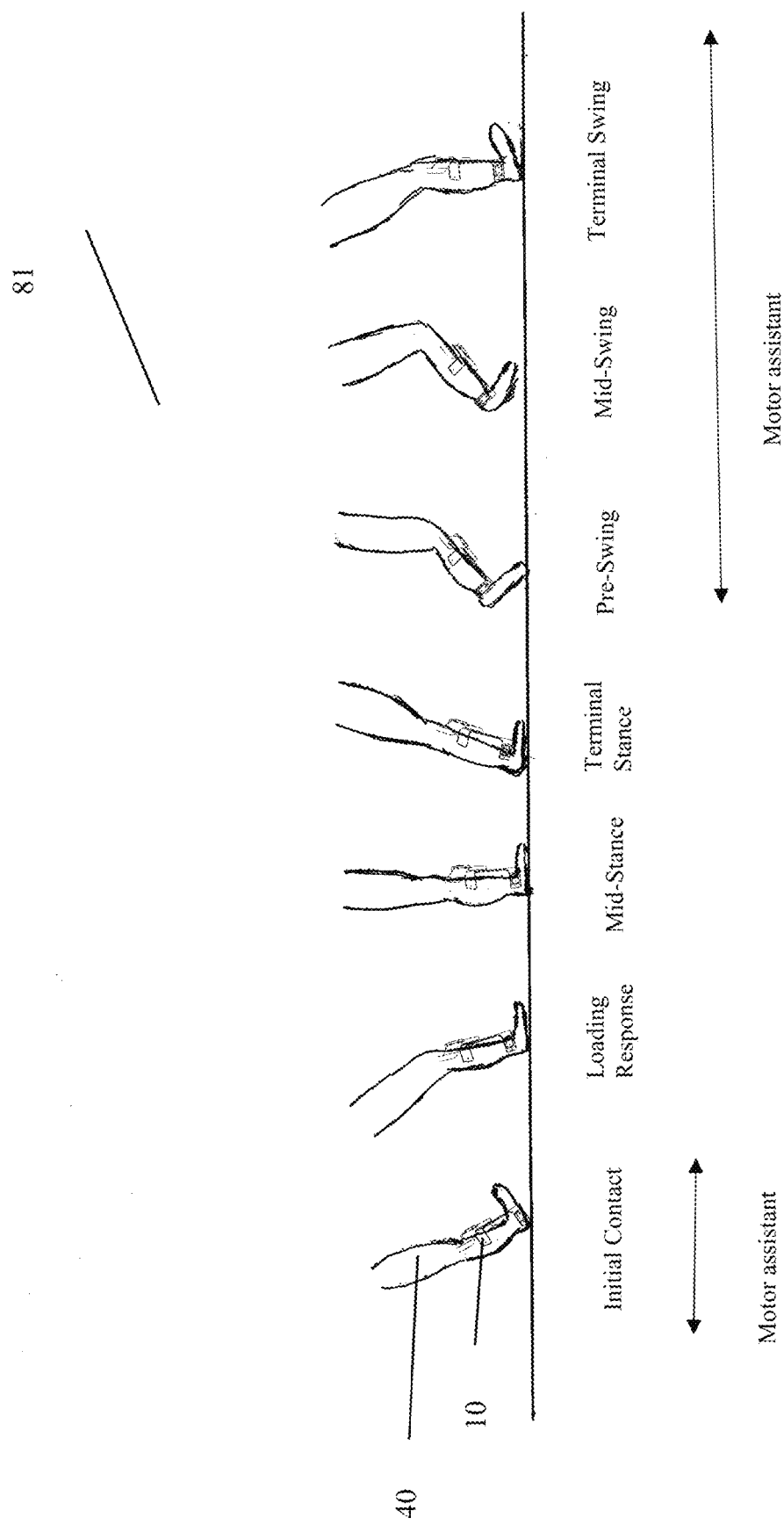
FIG. 12 is showing an example of the control actuator output at different gait phase according to an embodiment of the present invention.
Figure 13:
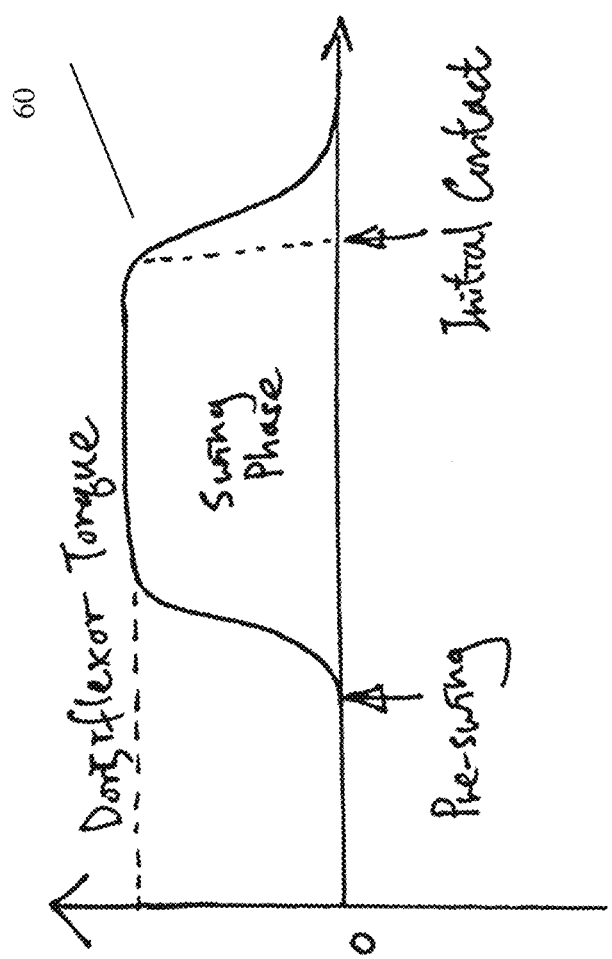
FIG. 13 is showing an example of the dorsiflexion torque from the motor at different gait phase according to an embodiment of the present invention.
Figure 14:
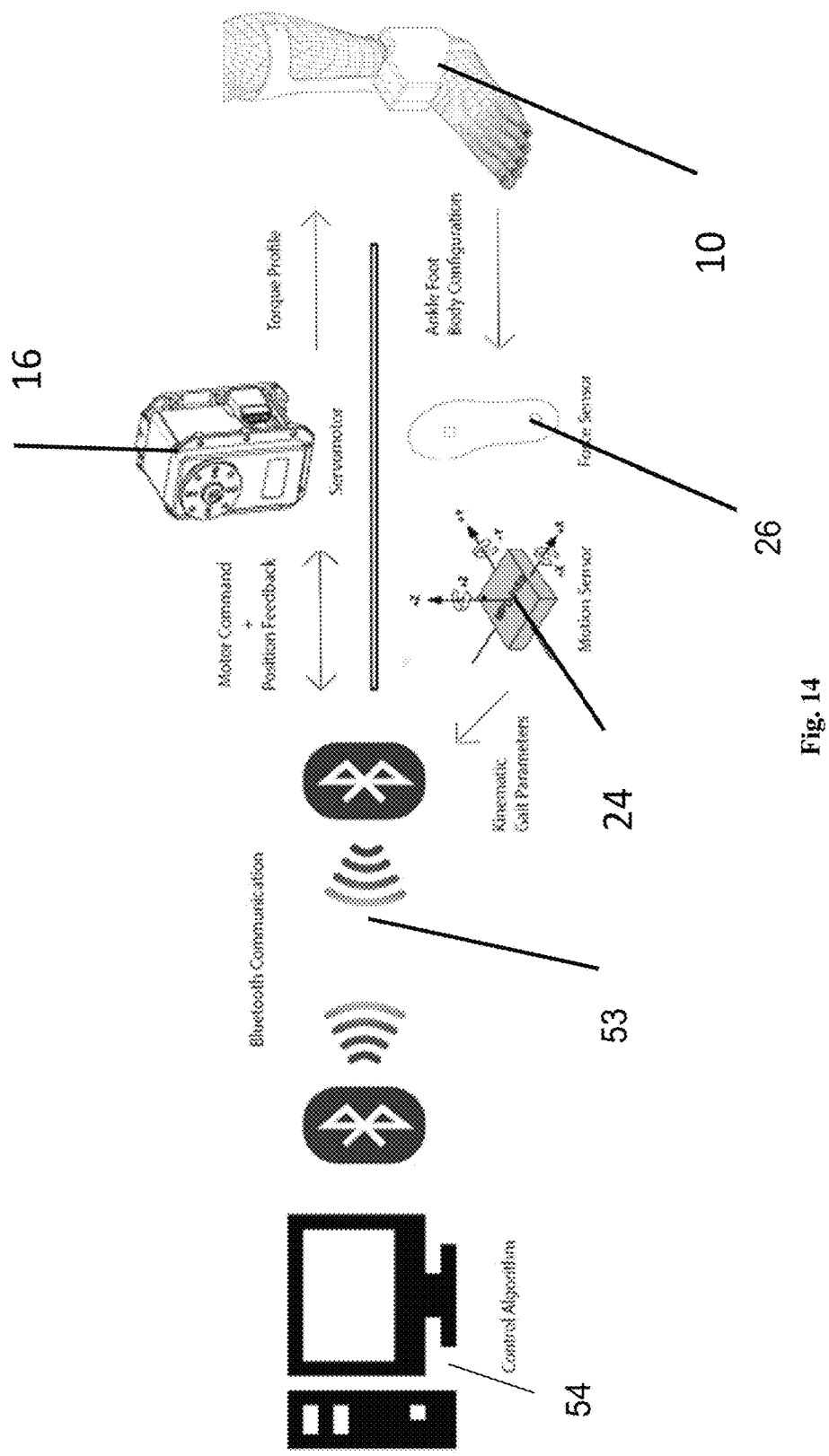
FIG. 14 is showing an example of wireless communication between the ankle robot and an external computer according to an embodiment of the present invention.
Figure 15:
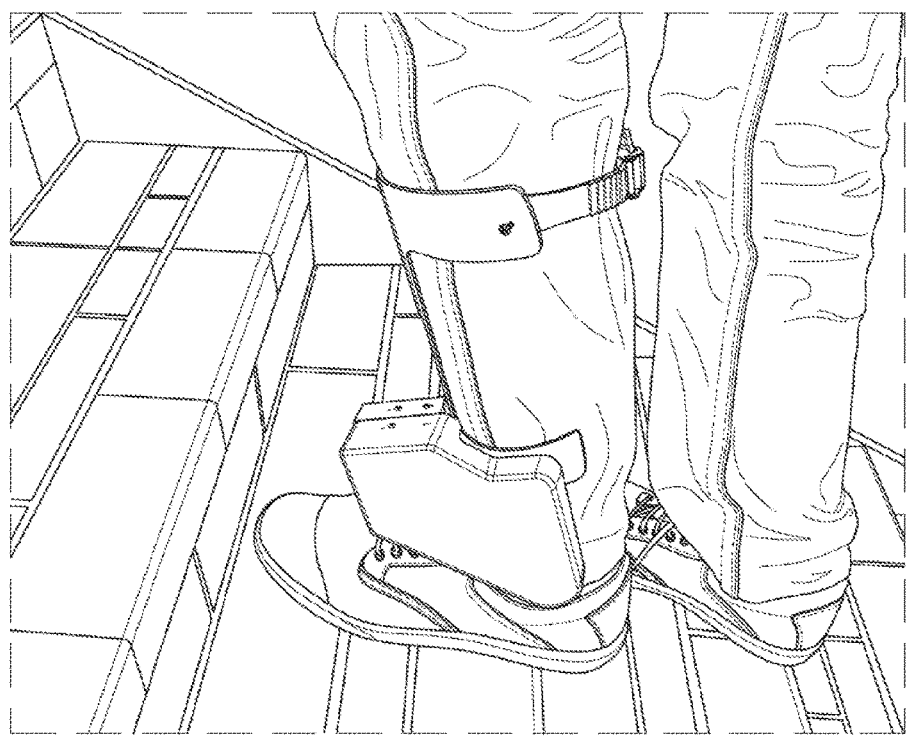
FIG. 15 is showing a side view of a user wears the ankle robot with his own unmodified shoe during stair ascend according to an embodiment of the present invention.
Figure 16:
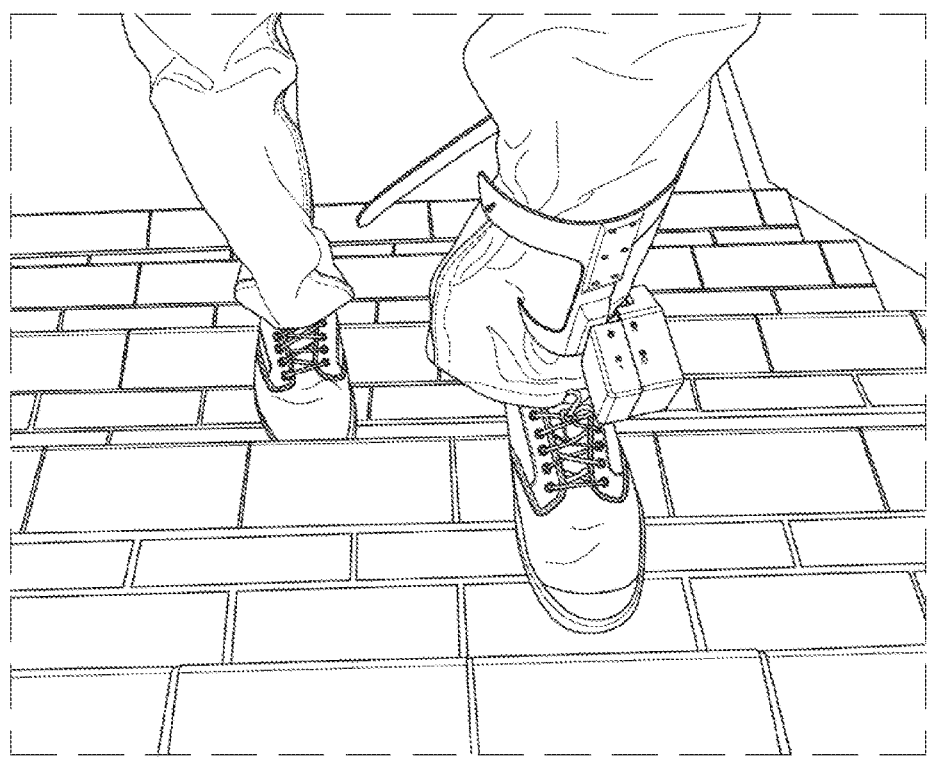
FIG. 16 is showing a front view of a user wears the ankle robot with his own unmodified shoe during stair ascend according to an embodiment of the present invention.
Figure 17:
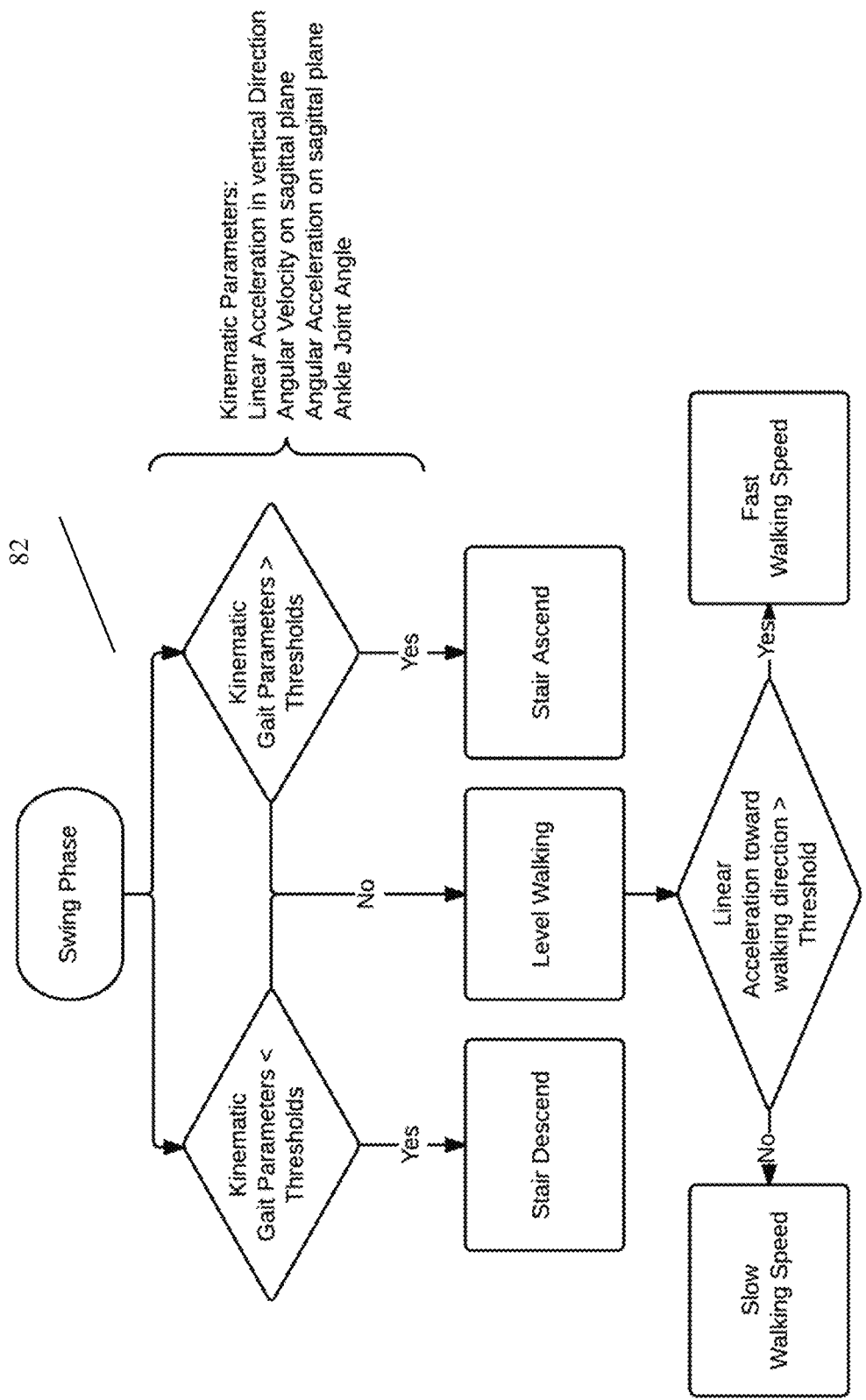
FIG. 17 is an example of a process flow diagram of the control algorithm to identify different walking environments and adjust the walking speed according to an embodiment of the present invention.
Figure 18:
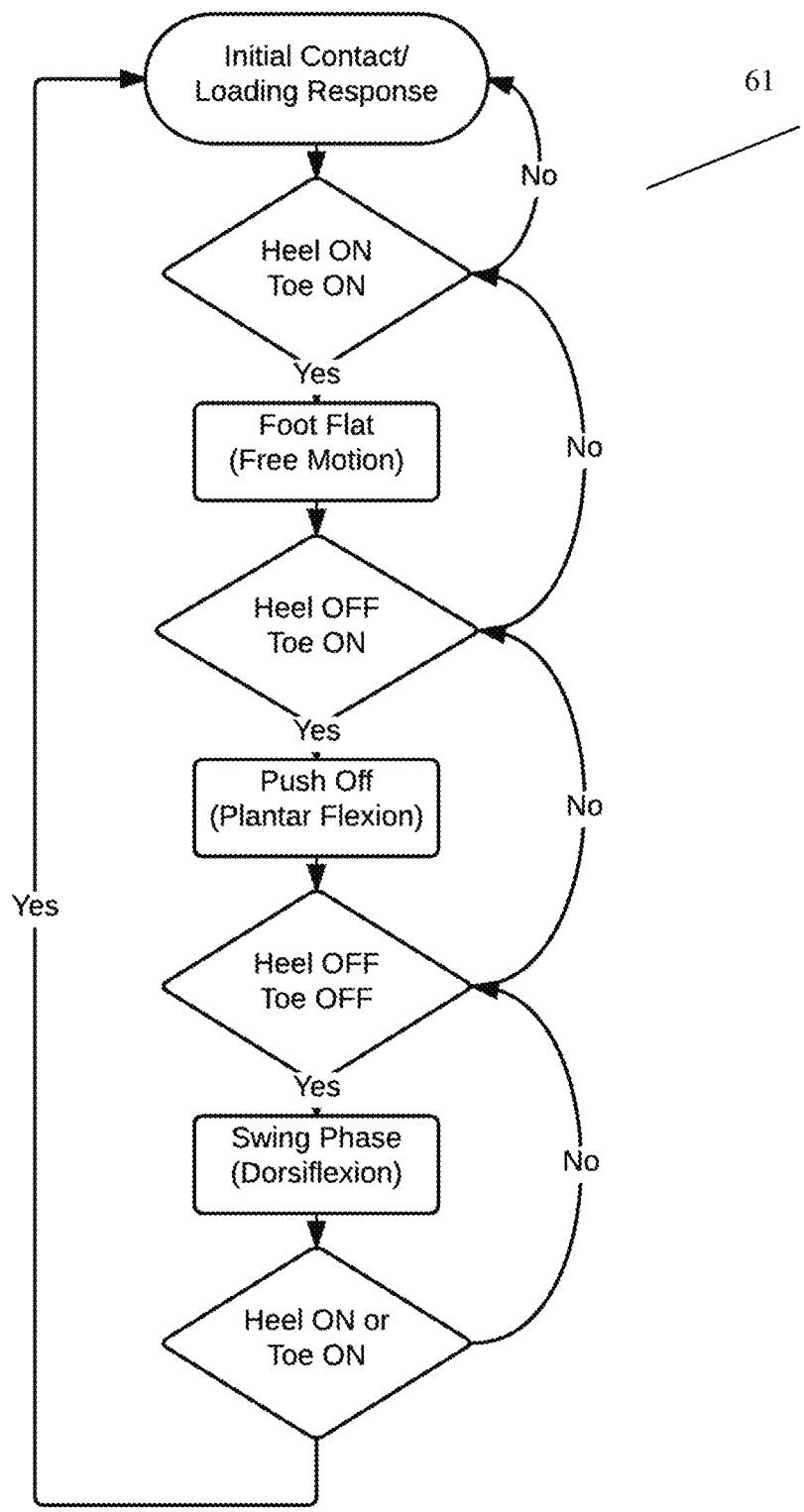
FIG. 18 is an example of a process flow diagram of the control algorithm to identify gait phases with foot contact pattern according to an embodiment of the present invention.

Referring to FIGS. 1 to 18, preferred embodiments of this invention will now be discussed in detail with respect to the drawings. The drawings include schematic figures that may not be to scale, which will be fully understood by skilled artisans with reference to the accompanying description.

The embodiment of this invention is an ankle robot 10 that has a compact and lightweight structure. Carbon fiber composites, fiber reinforced thermosetting plastic such as high-density poly-carbon, and lightweight metals such as aluminum and titanium are non-limiting candidates of material that can be used to fabricate the ankle robot 10. The ankle robot 10 has an articulated joint 23 that consists of two separated parts pivotally joined together at the ankle axis 11. The upper part is the leg brace 12 and the lower part is the foot piece 13. They can be custom fabricated to individual users by molding the contour of their ankle foot complex.

The leg brace 12 is a rigid structure covering the anterior shank from around an inch distal of lateral malleolus to at least an inch distal to fibular head to provide enough clearance for the joint movements. It is secured on the leg 40 of the user using fastening means 15. The fastening means 15 is secured onto the leg brace 12 using rivets 31. The fastening means 15 could be of any straps including but not limiting to Velcro fasteners or m2 Ratcheting Buckle and Ladder Straps. The foot piece 13 is coupled to the lower end of the leg brace 12 through an articulated joint 23.

The foot piece 13 is a mechanical structure supporting the foot of the user, with a proximal extension 22 on the lateral side up to the lateral malleolus for coupling with the articulated joint 23. It can be fit inside unmodified footwear without occlusion. The leg brace 12 and the foot piece 13 are preferably padded with cushion to avoid sharp edges hurting the body of the user and to absorb shock during walking. The height of the articular joint 23 from the level of the foot piece 13 can be adjusted with length adjustment 30 (three adjustments of 1 cm pitch in this example).

The articulated joint 23 is coupled with an actuation assembly that comprises an electrical rotatory motor 16 and a set of spur gears 17 18 19 20, and they are housed in a cover box 41. Electrical rotatory motor 16 is preferably a servomotor that can provide hybrid position and torque control, with joint angle feedback. It is fixed at the end of the leg brace 12 and engaged with the spur gear 17. The spur gears 18 19 20 could be meshed with the spur gear 17 in a consecutive order, for which another transmission mechanism such as belt drive is also contemplated. The first spur gear 17 has less number of teeth than the last spur gear 20, thus forming a gear ratio. A non-limiting example would be a 24-teeth first spur gear 17 and a 40-teeth last spur gear 20, which result in a gear ratio of 1.67. An example of an electrical rotatory motor 16 could provide up to 20.0 Nm torque, for which rotatory motor that could provide more than 20.0 Nm torque are also contemplated. After the torque amplification of the gear transmission system 17 18 19 20, the torque output could reach up to 33.4 Nm. The spur gears 17 18 19 20 configuration translates the axis of rotation of the electrical rotatory motor 16 to the anterior of the leg brace 12, where it would be less likely to occlude the other movable parts during gait of the user. The small electrical rotatory motor 16 requires low power source 28. Example power source would be a rechargeable lithium-ion polymer battery weights about 300 g. Total weight of the robot ankle 10 can be less than 1 kg.

This invention comprises a sensor system that includes at least one sensor integrated in the robot ankle to provide kinetic and kinematic feedback about the gait pattern of the user. Preferred embodiment of this invention has a motion sensor 24 placed on the leg brace 12, and a motion sensor 25 placed on the foot piece 13 to sense the change in displacement and orientation of the two parts of the ankle robot. With these two motion sensors, the spatial relationship between the shank and the foot, i.e. the ankle joint configuration, ankle angle, can be monitored. Force sensors 26 and 27 placed at the heel and forefoot of the foot piece 13 to sense the foot loading at the two portions of the foot for heel ON/OFF and toe ON/OFF respectively in the foot control algorithm 61. These two force sensors can be used as a foot contact pattern detector to identify the gait phase based on foot contact pattern 80 with a process flow diagram of the foot control algorithm 61 and implement with the ankle robot 10 during walking with a gait cycle pattern 81. A non-limiting example of the embodiment utilizes a motion sensor chip containing a tri-axial accelerometer and a tri-axial gyroscope. However, other sensors such as angle encoders, potentiometers, and flex sensors, can also be used. Force sensors are preferably thin force sensitive resistors, while force transducers, strain gauges can also be used. These sensors communicate with the on-board controller 29 to provide kinetic and kinematic feedback of gait pattern of the user. The on-board controller 29 is preferably microprocessor with memory of a control algorithm that controls the actuator output based on the kinetic and kinematic sensor feedback. Power source of the controller can be any suitable power source, such as but not limited to a 9V battery, two AA batteries, or the power source 28. The cable 61 transmits the power to the controller 29; the motor cable 63 transmits the power and signal between the controller 29 and the motor 16; the foot piece sensor cable 62 transmits the power and signal between the controller 29 and the sensor on the foot piece 13; and the shank sensor cable 64 transmits the power and signal between the controller 29 and the motion sensor 24 on the leg brace 12.

The control algorithm programmed into the on-board controller 29 controls the actuation of the articulated joint 23 of the device, so as to assist the gait of the user. The controller 29 receives kinetic and kinematic sensor feedback from the sensor system, including a change in displacement and orientation of the leg brace 12 and the foot piece 13, and a plantar force applying to the foot piece 13. The control algorithm processes the kinetic and kinematic sensory feedback, and determines a particular gait phase. At the particular gait phase, the control algorithm classifies the walking conditions by comparing the kinetic and kinematic sensory feedback with a set of predetermined thresholds. If the gait pattern exceeds the predetermined thresholds, it triggers the controller 29 to send a determined torque profile to the electrical rotary motor 16. The electrical rotary motor 16 will generate the determined torque profile for actuating the articulated joint 23. In this way, the ankle robot 10 can selectively assisting or braking the movement along the ankle joint axis 11 for facilitating the gait of the user. Walking conditions includes but not limited to different walking speeds and walking on different levels (over-ground walking, stair ascend, or stair descend). The flow diagram of the walking control algorithm 82 to identify different walking environments and walking speeds; and the motor torque assistance profile 60 can be implemented in the controller 29. The controller 29 can communicate with external electronic device using wireless communication 53.

To classify the walking conditions, the controller 29 determines the occurrence of a particular gait phase by comparing the received gait pattern feedback with a set of predetermined threshold. In a preferred embodiment, the set of predetermined threshold can be customized to individual users by calibrations before operation.

Since the stroke patients suffer from drop foot 70, the ankle joint is most likely in a plantar flexion configuration. During comfortable quiet standing, the ankle robot 10 is likely to have a large proportion of body weight loaded on the forefoot force sensor 27; as opposed to normal healthy ankle foot joint configuration that has both heel and forefoot receiving evenly distributed weight. The Kinetic thresholds of the force sensors 26 and 27 can be configured by performing a standing calibration before the device operation. Measurements from the two force sensors can be averaged. Example calibration might comprise a one-minute standing with body weight shifting from one side to another side at half a minute to measure the loading and unloading forces under the foot respectively. Then during operation, whenever the averaged force sensor feedback dropped below the unloading kinetic threshold, it could indicate terminal stance or pre-swing phase.

The motion sensors 24 and 25 can measure the kinematic sensor feedbacks, such as the ankle joint angle, the tilting angle, linear acceleration, and angular velocity of the body segments (shank and foot). These variables obtained in different walking conditions: walking speeds, walking levels, etc., can be inputted into an advanced classification model like the Support Vector Machine (SVM), Neural Network, or the Hidden Markov Model (HMM) to perform a machine learning process. An optimized classifier of the walking conditions can be obtained which can classify the walking conditions. Kinematic thresholds of the motion sensors 24 and 25 can be configured with a walking calibration before the device operation. The walking calibration might comprise a series of randomized walking trials with different walking conditions, repeated for at least 3 times for each condition.

The present invention further provides a system performed by the ankle robot of the present invention and the method of the present invention.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:
1. An exoskeleton ankle robotic device comprising:
a leg brace;
a foot piece pivotally coupling to said leg brace at or proximal to an ankle position;
an actuator coupling to said leg brace and said foot piece through an articulated joint, said actuator receiving power from a power source and generating a torque to drive said articulated joint to produce relative rotatory movement between said leg brace and said foot piece;
a gear transmission system coupling to said actuator and said articulated joint to transmit rotation axis of the actuator;
at least one force sensor for measuring force applied to the foot piece;
motion sensors comprising an accelerometer for measuring linear acceleration along a shank of a user and a gyroscope for measuring angular velocity of the shank of the user; and
a controller configured to:
receive the force applied to the foot piece for determining a gait phase of the user;
receive the linear acceleration and the angular velocity, both of which are measured at the gait phase; wherein the gait phase is either a swing phase or a pre-swing phase;
compare the linear acceleration and the angular velocity with a set of predetermined thresholds to classify a walking condition of the user using a control algorithm, the set of predetermined thresholds being determined under different walking conditions; and
send a command to control said actuator for actively assisting a gait of the user under the walking condition.

2. The exoskeleton ankle robotic device of claim 1, wherein the walking condition is overground walking, uphill, downhill, stair ascend, or stair descend.

3. The exoskeleton ankle robotic device of claim 2, wherein the control algorithm classifies the walking condition as the stair ascend when the linear acceleration is lower than a linear acceleration threshold from the set of predetermined thresholds and the angular velocity is lower than an angular velocity threshold from the set of predetermined thresholds.

4. The exoskeleton ankle robotic device of claim 2, wherein the control algorithm classifies the walking condition as the stair descend when the linear acceleration is higher than a linear acceleration threshold from the set of predetermined thresholds and the angular velocity is higher than an angular velocity threshold from the set of predetermined thresholds.

5. The exoskeleton ankle robotic device of claim 2, wherein the control algorithm classifies the walking condition as the overground walking when the linear acceleration is between a first linear acceleration threshold and a second linear acceleration threshold from the set of predetermined thresholds.

6. The exoskeleton ankle robotic device of claim 1, wherein said gear transmission system comprises at least one pair of gears, said at least one pair of gears translating the axis of rotation to a location away from or proximal to said ankle position.

7. The exoskeleton ankle robotic device of claim 6, wherein said location is anterior to the shank of the user.

8. The exoskeleton ankle robotic device of claim 6, wherein said at least one pair of gears has a gear ratio, said gear ratio amplifying or diminishing a torque transmitting across said gear transmission system.

9. The exoskeleton ankle robotic device of claim 1, wherein said actuator comprises a servomotor providing torque control or position control to said articulated joint.

10. The exoskeleton ankle robotic device of claim 1, wherein said power source is a battery.

11. The exoskeleton ankle robotic device of claim 1, wherein said leg brace and said foot piece comprise rigid and lightweight materials selected from a group consisting of carbon fiber, carbon composite, light metal, and plastic.

12. The exoskeleton ankle robotic device of claim 1, wherein said controller comprises a microprocessor and a memory.

13. The exoskeleton ankle robotic device of claim 1, wherein said controller is further configured to communicate with an external computing device through a wireless communication network.

14. The exoskeleton ankle robotic device of claim 1, wherein said at least one force sensor is selected from a group consisting of a force sensitive resistor, a force transducer, and a strain gauge.

15. The exoskeleton ankle robotic device of claim 1, wherein said motion sensors further comprise an angle encoder, a potentiometer, or a flex sensor.

16. The exoskeleton ankle robotic device of claim 1, wherein the controller is further configured for determining a walking speed of the user.

* * * * *